United States Patent [19]

Fernandez-Pol

[11] Patent Number: 5,767,135
[45] Date of Patent: Jun. 16, 1998

[54] ANTIVIRAL AGENT

[76] Inventor: Jose Alberto Fernandez-Pol, 437 Hunters Hill Dr., Chesterfield, Mo. 63017

[21] Appl. No.: 581,351

[22] Filed: Dec. 29, 1995

[51] Int. Cl.$^6$ .................................................. A61K 31/44
[52] U.S. Cl. .................................................. 514/354
[58] Field of Search .................................................. 514/354

[56] References Cited

U.S. PATENT DOCUMENTS

| | | | |
|---|---|---|---|
| 4,044,140 | 8/1977 | Sherlock | 514/354 |
| 4,814,351 | 3/1989 | Mathews et al. | 514/566 |
| 5,219,847 | 6/1993 | Taguchi et al. | 514/188 |

OTHER PUBLICATIONS

Lyons, J.M. et al, Clin. Infect. Dis. 1995(Oct.), 21 Suppl. 2, S174–S177. abstract.

J. A. Fernandez–Pol, Isolation and Characterization of a Siderophore–Like Growth Factor from Mutants of SV40–Transformed Cells Adapted to Picolinic Acid, Cell vol. 14, 489–499, Jul. 1978.

J. A. Fernandez–Pol et al., Control of growth by picolinic acid: Differential response of normal and transformed cells; Cell Biology; vol. 74, No. 7 pp. 2889–2893, Jul. 1977.

John J. Collins, et al., Transient Growth Inhibition of *Escherichia coli* K–12 by Ion Chelators: "In Vivo" Inhibition of Ribonucleic Acid Synthesis; Journal of Bacteriology, Jun. 1979 pp. 923–932.

J. A. Fernandez–Pol; Morphological Changes Induced by Picolinic Acid in Cultured Mammalian Cells; Experimental and Molecular Pathology 29; 348–357 (1978).

J. A. Fernandez–Pol et al., NRK Cells Synchronized In $G_1$ By Picolinic Acid Are Super–Sensitive Prostaglandin $E_1$ Stimulation, vol. 74, No. 2; Febs Letters, Mar. 1977.

J. A. Fernandez–Pol, Peptide and Protein Complexes of Transition Metals as Modulators of Cellular Replication; International Journal of Nuclear Medicine and Biology vol. 8. pp. 231–235 (1981).

J. A. Fernandez–Pol et al., Iron Transport In NRK Cells Synchronized In $G_1$ By Picolinic Acid, Cell Biology International Reports, vol. 2, No. 5, pp. 433–439 (1978).

J. A. Fernandez–Pol, Iron: Possible Cause of the $G_1$ Arrest Induced In NRK Cells By Picolinic Acid; Biochemical And Biophysical Research Communications, vol. 78, No. 1, pp. 136–143, 1997.

J. A. Fernandez–Pol, Transition Meal Ions Induce Cell Growth In NRK Cells Synchronized In $G_1$ By Picolinic Acid, vol. 76, No. 2, Biochemical And Biophysical Research Communications pp. 413–419 (1977).

J. A. Fernandez–Pol et al., Selective Toxicity Induced by Picolinic Acid in Simian Virus 40–transformed Cells in Tissue Culture, Cancer Research 37, 4276–4279, (Dec. 1977).

Michael L. Gargas et al. Urinary Excretion of Chromium by Humans Following Ingestion of Chromium Picolinate; Drug Metabolism and Disposition, vol. 22, No. 4 pp. 522–529 (1994).

Letter to the Editor; Chromium Picolinate is an Efficacious and Safe Supplement; International Journal of Sport Nutrition, 1993 pp. 117–122, 1993 Human Kinetics Publishers Inc.

Dennis J. Bobilya et al., Ligands Influence Zn Transport into Cultured Endothelial Cells, pp. 159–166.

Stephen P. Clancy et al., Effects of Chromium Picolinate Supplementation on Body Composition, Strength, and Urinary Chromium Loss in Football Players; Original Research, International Journal of Sport Nurtition, 1994 142–153 1994 Human Kinetics Publishers, Inc.

G. W. Evans et al. Composition and Biological Activity of Chromium–Pyridine Carboxylate Complexes, Journal of Inorganic Biochemistry 49, pp. 177–187 (1993).

G. W. Evans et al., Chromium Picolinate Increases Membrane Fluidity and Rate of Insulin Internalization, Journal of Inorganic Biochemistry 46, pp. 243–250 (1992).

Nancy A. Lee et al., Beneficial Effect of Chromium Supplementation on Serum Triglyceride Levels in NIDDM, Diabetes Care vol. 17 No. 12 Dec. 1994.

M.D. Lindemann[2] Dietary Chromium Picolinate Additions Improve Gain:Feed and Carcass Characteristics in Growing–Finishing Pigs and Increase Litter Size in Reproducing Sows[1] ; J. Anim. Sci. 1995 73: 457–465.

An Inexpensive, Convenient Adjunct for the Treatment of Diabetes, The Western Journal of Medicine Nov. 1991 p. 549.

T.G. Page et al. Effect of Chromium Picolinate on Growth and Serum and Carcass Traits of Growing–Finishing Pigs[1,2,3] J. Anim. Sci. 1993 71:656–662.

Raymond I. Press, MD, et al., The Effect of Chromium Picolinate on Serum Cholesterol and Apoliprotein Fractions in Human Subject, West J Med 1990 Jan.; 152:41–45.

Medline Search May 28, 1996.

L. Varesio et al., Ribosomal RNA Metabolism in Macrophages, Current Topics In Microbiology and Immunology vol. 181 1992.

T.L. Varadinova et al., Mode of Action of Zn–Complexes on Herpes Simplex Virus Type 1 Infection In Vitro, Journal of Chemotherapy, vol. 5, 3–9 1993.

J. Cockhill et al., Action of picolinic acid and structurally related pyridine carboxylic acids on quinolinic acid–induced cortical cholinergic damage; Brain Research 599 (1992) 57–63.

(List continued on next page.)

*Primary Examiner*—C. Warren Ivy
*Assistant Examiner*—Garth M. Dahlen
*Attorney, Agent, or Firm*—Polster, Lieder, Woodruff & Lucchesi

[57] ABSTRACT

An antiproliferative and antiviral preparation of a metal ion chelating agent such as picolinic acid or derivatives thereof. The chelating agent is provided in an ointment base or in solution for topical or intravaginal use. The topical preparations have antiviral and antiproliferative effects and are used in the treatment of warts, psoriasis, skin cancers and other proliferative diseases and in the prevention of sexually transmitted diseases such as genital warts, herpes and AIDS.

18 Claims, 4 Drawing Sheets

OTHER PUBLICATIONS

Bettina E. Kalisch et al., Picolinic acid protects against quinolinic acid–induced depletion of NADPH diaphorase containing neurons in the rat striatum; Brain Research 668 (1994) 1–8.

R.J. Beninger et al., Picolinic Acid Blocks the Neurotoxic but not the Neuroexcitant Properties of Quinolinic Acid in the Rat Brain: Evidence from turning behavior and tysosine hydroxylase immunohistochemistry Neuroscience vol. 61. No. 3 pp. 603–612, 1994.

R.J. Boegmanet al., Neurotoxicity of Tryptophan Metabolities; Annals New York Academy of Sciences vol. 585 1990 pp. 261–273.

L. Vrooman et al., Picolinic Acid modulates kainic acid–evoked glutamate release from the striatum in vitro; Brain Research 627 (1993) 193–198.

Elisabetta Blasi et al., Protective Effect of Picolinic Acid on Mice Intracerebrally Infected with Lethal Doses of *Candida albicans*; Antimocrobial Agents and Chemotherapy, Nov. 1993 pp. 2422–2426 vol. 37, No. 11.

Giovanni Melillo et al., Regulation of Nitric–oxide Synthase mRNA Expression by Interferon–γ and Pocolinic Acid, The Journal of Biological Chemistry vol. 269, No. 11 Issue of Mar. 18, pp. 8128–8133, 1994.

Elisabetta Blasi et al., Inhibition of Retroviral MRNA Expression In The Murine Macrophage Cell Line GG2EE by Biologic Response Modifiers[1] ; The Journal of Immumology vol. 141 pp. 2153–2157 No. 6 Sep. 15, 1988.

Takashi Mikagami et al., Effect of intracellular iron depletion by picolinic acid on expression of the lactorferrin receptor in the human colon carcinoma cell subclone HT29–18$C_1$; Biochem J. (1995) 308 391–397 (Printed In Great Britian).

George W. Cox et al., IL–4 Inhibits the Costimulatory Activity of IL–2 Or Pocolinic Acid But Not Of Lipopolysaccharide on IFNγ Treated Macrophages; The Journal of Immunology vol. 147 3809–3814 No. 11, Dec. 1, 1991.

Elisabetta Blasi et al., Pattern of cytokine gene expression in brains of mice protected by picolinic acid against lethal intracerebral infection with *Candida albicans*; Journal of Neuoimmumology 52 (1994) 205–213.

Giovanni Melillo, Picolinic Acid, a Catabolite of L–Tryptophan, Is a Costimulus for the Induction of Reactive Nitrogen Intermediate Production in Murine Macrphages; The Journal of Immumology vol. 150 4031–4040 No. 9 May 1, 1993.

Ann M. Bode et al., Inhibition of glucose–6 phosphate phosphohydrolase by 3–mercaptopicolinate and two anologs is metabolically directive; Biochem Cell Biol, vol. 71, 1993 pp. 113–121.

Balducci et al., Geriatric Oncology; 1992; Chapter 7 Growth Factors, Oncogenes, Antionacogenes and Aging; pp. 60–75.

Ensoli et al., Tat protein of HIV–1 stimulates growth of cells derived from Kaposi's sacroma lesions of AIDS patients; Nature; May 3, 1990; pp. 84–86.

Frankel et al.,; Cellular Uptake of the Tat Protein from Human Immunodeficiency Virus; Cell; vol. 55, pp. 1189–1193; Dec. 23, 1988.

Fernandez–Pol et al., Cytotoxic Activity of Fusaric Acid on Human Adenocarcinoma Cells in Tissue Culture; 1993 Anticancer Research 13: pp. 57–64.

FIG. 5A
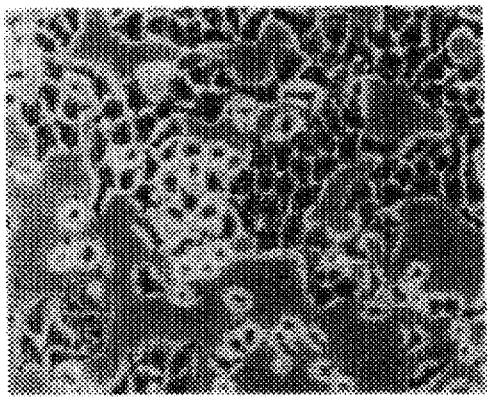
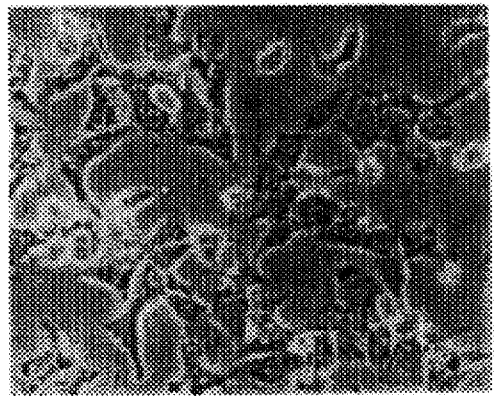
FIG. 5B

ANTIVIRAL AGENT

BACKGROUND OF THE INVENTION

The invention relates to the treatment of spontaneous and viral-induced proliferative diseases. More specifically the invention relates to the use of metal chelating materials including, picolinic acid, fusaric acid and their derivatives as a chemotherapeutic and/or biological response modifier agents.

Papilloma virus infection results in a number of proliferative diseases including warts induced by type 4 human papilloma virus (common warts). Moreover, papilloma virus can cause plantar ulcers as well as plantar warts. Human papilloma virus infection of the uterine cervix is the most common of all sexually transmitted diseases. Commonly know as genital warts, this wide spread virus infection is a serious disease that potentially can develop into cervical cancer. Since the virus is permanently present in cells, infection recurs in a significant percentage of patients. In many instances, conization of the uterine cervix is required to remove the infected tissue.

*Condylomata acuminata*, also denoted genital warts, are benign epithelial growths that occur in the genital and perianal areas and caused by a number of human papilloma viruses (HPV) including types 6,11 and 54. These are low risk viruses which rarely progress to malignancy. However, high risk viruses such as HPV-16 and HPV-18 are associated with cervical intraepithelial cancer.

The actions of HPV are mediated by specific viral-encoded proteins which interact and/or modulate cellular DNA and proteins to produce abnormal growth and differentiation of cells. Two proteins of the HPV viral genome, E6 and E7, are well conserved among anogenital HPV's and both may contribute to the uncontrolled proliferation of basal cells characteristics of the lesions. The E7 oncoprotein is a multifunctional protein with transcriptional modulatory and cellular transforming properties. The E7 oncoprotein is denoted as a "zinc finger" protein because it pocesses a sequence motif that is implicated in zinc binding. A strong correlation between zinc binding and the transactivation activity of E7 has been documented. The HPV-16 E6 protein is a "zinc finger" protein that binds DNA and may have transcriptional properties and that function may be dependent upon the formation of zinc fingers. E6 can complex with the cellular tumor suppressor protein p53 and it is necessary with E7 for the immortalization of primary human squamous cells.

The human immunodeficiency virus (HIV) encodes several regulatory proteins that are not found in other retroviruses. The tat protein, which is one of these proteins, trans-activates genes that are expressed from the HIV long terminal repeat and tat is essential for viral replication. The tat protein of the HIV-1 is a zinc finger protein that when added to certain cells in tissue culture, specifically promotes growth. It has been shown that the tat protein of HIV-1 stimulates growth of cells derived from Kaposi's sarcoma lesions of AIDS patients. Other experiments raised the possibility that tat might act as a viral growth factor to stimulate replication in latently infected cells or alter expression of cellular genes.

From the foregoing it appears that it would be beneficial to have a product that can interfere with the formation or action of certain zinc finger proteins to as to stop the progress of certain virally induced or mediated proliferative diseases or to halt the progress of viruses dependent upon zinc finger proteins for their transformation and immortalization. Furthermore, it would be beneficial to provide a product that can halt the growth of other proliferative cells, such as malignant cells by chelating metal ions from zinc-dependent proteins and enzymes necessary for the replication or transcription of the malignant cells.

SUMMARY OF THE INVENTION

It is among the objects of the present invention to provide a compound which can retard the growth and proliferation of target cells.

It another objects of the present invention to provide a compound that can retard the growth of premalignant and malignant cells such as virally, chemically and spontaneously transformed cells.

It is also among the objects of the present invention to provide a new treatment for patients suffering from various forms of spontaneous and retroviral-induced proliferative diseases and cancers by utilizing the novel properties of metal chelating agents as a chemotherapeutic/anti-viral agent and/or biological response modifier.

It is another object of the invention to provide a method of halting the function of zinc finger proteins by the administration of a zinc chelating agent.

Yet another object of the invention is to provide such chelating agents in a relatively safe and nontoxic form such as picolinic acid and its derivatives.

Another object of the invention is to provide a topical preparation of metal chelating agents such as picolinic acid or its derivatives to treat virally induced or spontaneous proliferative diseases of the skin or mucous membranes.

It is still another object of the present invention to provide an intravaginal preparation containing metal chelating agents such as picolinic acid or derivatives thereof that can prevent or retard sexually transmitted diseases caused by viruses containing zinc finger proteins.

Still another object of the present invention is to provide a preparation containing chelating agents such as picolinic acid or derivatives thereof that halts the progression of viral infections or proliferative diseases that is non-toxic to normal cells, easy to use, relatively inexpensive and well suited for its intended purposes.

According to the invention, briefly stated, a preparation containing metal chelating compounds, for example picolinic acid or derivative thereof, used to treat viral or proliferative diseases, as well as the method of treatment. The preparation can be used to treat or control a wide assortment of proliferative diseases or conditions, both spontaneous or virally induced. The metal chelating compounds bind metal, for example iron or zinc, required by enzymes or by transcription proteins found in viruses or malignant cells.

One embodiment of the preparation consists of a solution of the chelator, for example, 0.5 to 50%, preferably 5% to 25%, picolinic acid in deionized water and is applied to the lesion one or two times a day. In another embodiment, the preparation consists of an ointment or cream containing approximately 0.5% to 50%, preferably 5% to 20% picolinic acid which is applied once or twice daily to the lesion and to a bandage placed on the lesion. The ointment or cream can be instilled intravaginally to retard sexually transmitted viral diseases. The various embodiments can be used to treat papilloma and herpes viral diseases and to retard the papilloma, herpes and HIV 1 viruses as well as proliferative diseases such as psoriasis and skin cancer.

It will be appreciated that other appropriate chelating materials such as the derivative of picolinic acid, fusaric acid, also may be used. It also will be appreciated that, although 5% to 20% preparations of the picolinic acid are described, a broader range of concentrations may be used. For example from approximately 0.5% to 50% or greater metal chelating agent may be used.

BRIEF DESCRIPTION OF THE DRAWINGS

FIG. 5A illustrates the effects of fusaric acid on morphology of KB cells, the cells treated without fusaric acid; and FIG. 5B illustrates the effects of fusaric acid on morphology of KB cells, the cells treated with fusaric acid.

DETAILED DESCRIPTION OF THE INVENTION

Picolinic acid, a metal chelating, naturally occurring, biological compound, inhibits the growth of numerous cultured normal and transformed mammalian cells. It has been shown that short-term treatment with picolinic acid arrests normal cells in $G_1$, (Go) while transformed cells are blocked in different phases of the cell cycle. With longer exposure to picolinic acid cytotoxicity and cell death was observed in all transformed cells whether they were blocked in $G_1$, $G_2$ or at random. In contrast, most normal cells showed no toxic effects from the picolinic acid. Thus, the selective growth arrest and the differential cytotoxicity induced by picolinic acid reveals a basic difference in growth control and survival mechanism(s) between normal and transformed cells.

Kinetic and radiosotopic studies show that picolinic acid both inhibits incorporation of iron into the cells and effectively removes radioiron from the cells.

Hence, it is conceivable that the inhibition of cell proliferation in vitro, as well as tumor growth in vivo, by picolinic acid results, at least in part, from selective depletion of iron in the cells.

However, it also is shown that picolinic acid may arrest prokaryote and eukaryote cell growth by inhibiting Zn-requiring enzymes. In addition to its chelating ability, picolinic acid has a number of biologic properties such inhibitory effects on ADP ribosylation and ribosomal RNA maturation, modulation of hormonal responses, and macrophage activation. Picolinic acid in combination with interferon gamma can inhibit retroviral J2 mRNA expression and growth in murine macrophages. Thus, picolinic acid and its derivatives can act as a biological response modifier.

Fusaric acid is a potent inhibitor of cancerous cell growth. Fusaric acid, a picolinic acid derivative, metal ion chelator, shows an effect on the growth and viability of normal and cancerous cells in tissue culture. Examples presented here show that fusaric acid has potent anti-cancer and anti-viral activity in vitro. Moreover, fusaric acid may be useful in the treatment of spontaneous and virally-induced tumors in vivo without substantially damaging living normal cells.

Figure 1:
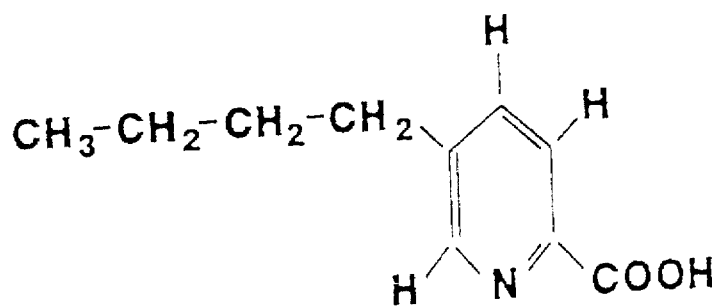
FIG. 1 is the chemical structure of fusaric acid.

Fusaric acid is the 5-butyl derivative of picolinic acid. Its structure is shown in FIG. 1. Fusaric acid was recognized in the early 1960's to have activity as an antihypertensive agent in vivo. Fusaric acid and its properties can be summarized as follows. Undoubtedly the drug interacts with various metaloproteins and metal ion-requiring enzyme systems. Fusaric acid is noted to be an inhibitor of a wide variety of seemingly unrelated enzyme systems. These include poly ADP ribose polymerase, a Zn-finger enzyme, and other Zn-finger proteins. Cu-requiring systems are also effected by fusaric acid. These enzymatic systems are important in growth control mechanisms. It has become increasingly clear that fusaric acid, by virtue of its butyl group penetrates the cell interior much more easily than picolinic acid, and works at least in part as a Zn/Cu chelating agent.

Examples of the specific effects of metal chelating agents, including picolinic acid and fusaric acid, as well as the practical application of those agents will now be described.

INHIBITION OF CELL GROWTH IN TISSUE CULTURE

EXAMPLE 1

Effects of Picolinic Acid on Growth of WI-38, LoVo and KB. Cells

Cells were plated at $1.5 \times 10^5$ cells/60-mm dish; 48 hours later, the medium was removed, and new media with or without 3 mM picolinic acid were added. Total cell protein was determined at the indicated times; each point is the average of triplicate measurements from 2 cultures.

The growth of normal WI-38 cells was inhibited by 3 mM picolinic acid within 24 hours, the cells showed no toxic effects for up to 72 hours of treatment, and the inhibition was reversible within 24 hours of removal of the agent (data not shown). These results are identical to previous results with WI-38 cells incubated with picolinic acid.

Figure 2:
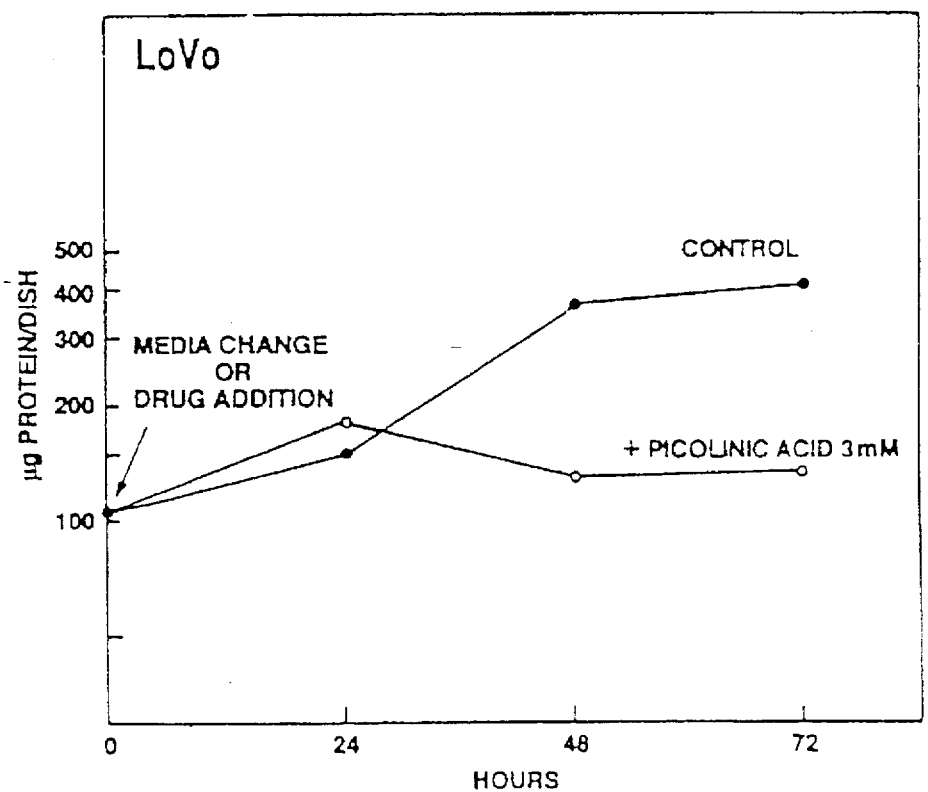
FIG. 2 illustrates the effect of picolinic acid on total protein of LoVo cells.

The growth of LoVo cells was inhibited by 3 mM picolinic acid (FIG. 2). After 24 to 48 hours of exposure to picolinic acid (3 mM), LoVo cells acquired a flattened morphology, they began to look granular, no mitosis were observed, and some began to float in the medium, (data not shown). With longer exposure (48–72 hours) cytotoxicity and cell death was observed in LoVo cells (data not shown). Equivalent results were obtained with cancerous KB cells treated with picolinic acid (3 mM) but its cytotoxic effects on this cell type were not as pronounced as in the case of LoVo cells (data not shown).

EXAMPLE 2

Effect of Fusaric Acid on Growth and Viability of Normal WI-38 cells.

In initial experiments to examine the effects of fusaric acid on cell growth and viability, WI-38 and LoVo cells were incubated for 24 to 72 hours in medium with or without various doses of fusaric acid (0.1–1 mM). The growth of both WI-38 and LoVo cells was inhibited by 500 µM fusaric acid in a time and dose dependent manner, as shown below in Table 1. A higher dose of fusaric acid (1 mM), caused a pronounced decrease in the rate of cell growth of both cell lines, and extensive cytotoxicity was noted particularly in LoVo cells by 24 hours. These preliminary experiments led to detailed tests of the effects of the highest dose of fusaric acid (500 µM) which appeared to show some differential toxicity on LoVo cells with little toxicity to WI-38 cells (Table 1).

TABLE 1

Effect of Different Doses of Fusaric Acid on WI-38 and LoVo Total Cell Protein

| Addition | Monolayer Protein (µg/dish)[a] | | | |
|---|---|---|---|---|
| | 0 h | 24 h | 48 h | 72 h |
| WI-38 | | | | |
| None | 105 | 202 | 270 | 371 |
| Fusaric acid (0.5 mM) | — | 195 | 275 | 345 |
| Fusaric acid (1 mM) | — | 236 | 202 | 195 |
| LoVo | | | | |
| None | 202 | 270 | 352 | 457 |
| Fusaric acid (0.5 mM) | — | 135 | 90 | 101 |
| Fusaric acid (1 mM) | — | ND | ND | ND |

[a]Cells were plated at 1.5 × 10[5] cells/60-mm dish in DME-F12 medium containing 10% Calf serum. The medium was removed 24 hours later and then fresh media containing the indications concentrations of fusaric acid were added. Protein was determine at the indicated times. Points are the mean of duplicate determinations. SE did not exceed 5% of the mean. ND, not done because of extensive cell destruction.

Figure 3A:
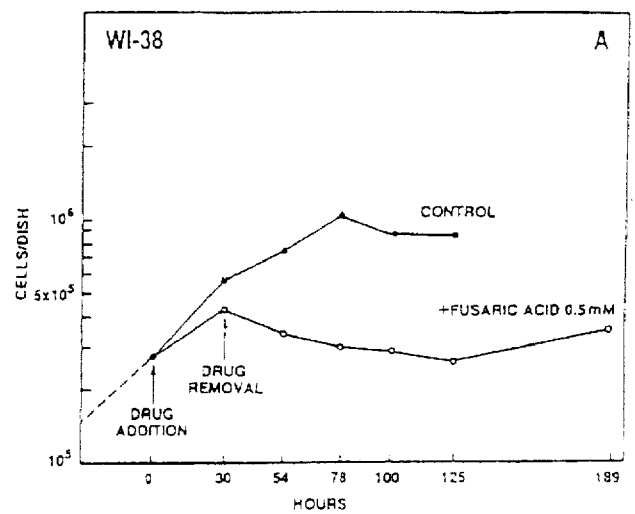
FIG. 3A illustrates the effects of fusaric acid on the growth of WI-38 cells.
Figure 3B:
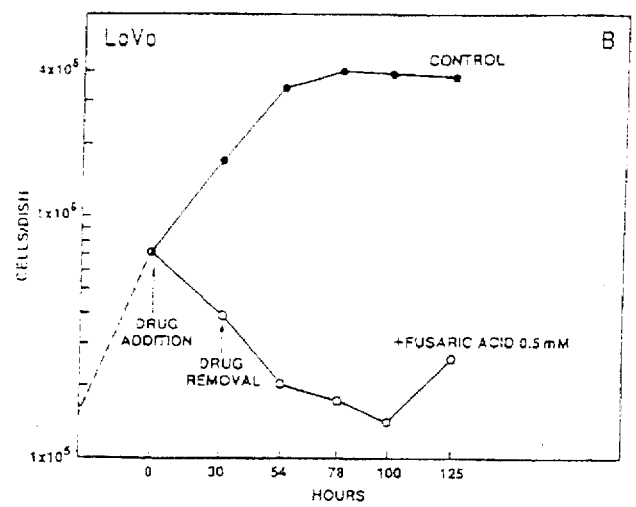
FIG. 3B illustrates the effects of fusaric acid on the growth LoVo cells.

FIG. 3A shows that the growth of WI-38 cells was strongly inhibited by 500 µM fusaric acid. After 30 to 48 hours in 500 µM fusaric acid, WI-38 cells acquired a more flattened morphology, showed some granularity, and no mitotic cells, as illustrated in FIG. 3B, or further increase in cell number were observed (See, FIG. 3A). Following 30 hours incubation with fusaric acid (500 µM), normal growth rate was not restored after removal of fusaric acid and the cell number decreased significantly (30%) after 4 days in normal media. The remaining cells were spread on the substratum in normal manner without any visible mitosis for 4 days after removal of the drug. However, they resumed growth after 125 hours of removal of fusaric acid (FIG. 3A), and most (>95%) of the cells survived. These results suggest that the majority of WI-38 cells were arrested in $G_1(G_o)$ by fusaric acid and they proceeded slowly through the cell cycle after its removal.

To examine WI-38 cell viability in greater detail, the effects of fusaric acid were studied in logarithmically growing and contact inhibited confluent cells (Tables 2 and 3). In logarithmically growing WI-38 cells approximately 76% of the cells were viable after 30 hours of treatment with fusaric acid. When the cells were treated for 78 hours, only 26% of the cell population survived the pronounced cytotoxic actions of fusaric acid The data are shown below in Table 2.

TABLE 2

Viability of Cells in Logarithmic Growth After Treatment with Fusaric Acid[d]

| Cell line | % Survival[b] | |
|---|---|---|
| | 30 h | 78 h |
| WI-38 | | |
| Control | 100 | 100 |
| Treated | 76.4 | 26 |

TABLE 2-continued

Viability of Cells in Logarithmic Growth After Treatment with Fusaric Acid[d]

| Cell line | % Survival[b] | |
|---|---|---|
| | 30 h | 78 h |
| LoVo | | |
| Control | 100 | 100 |
| Treated | 38.5 | 4.5 |

[d]The cells were incubated in medium with or without 500 µM fusaric acid for the indicated times.
[b]Fraction of total cells counted which did not stain with trypan blue. Cells attached to the dish were exposed to trypan blue and counted. The percentage exclusion by untreated cultures was normalized to 100% for comparison with fusaric acid-treated cultures.

The detach cells showed conspicuous cytotoxic effects and most of them were destroyed. Interestingly, in confluent cell, fusaric acid did not show any cytotoxic effects as determined by the fact that 100% of the cells survived 48 hours of treatment with 500 µM fusaric acid, as shown in Table 3, below.

TABLE 3

Viability of Confluent Cells after Treatment with Fusaric Acid (500 µM)

| Cell line | % Survival[a] | |
|---|---|---|
| | Control | Treated |
| WI-38 | 100 | 100 |
| LoVo | 100 | 40 |
| KB | 100 | 95 |

[a]Determined at 48 h using trypan blue dye exclusion test as indicated in Table 2.

Thus, a significant proportion of the population of growing cells (76%) and all of the confluent WI-38 cells cell resisted the marked cytotoxic action of fusaric acid.

EXAMPLE 3

Effect of Fusaric Acid on Growth and Viability of Colon Carcinoma LoVo Cells.

Fusaric acid (500 µM) inhibited LoVo cell growth, as shown in FIG. 3B. After 30 hours of treatment with 500 µM fusaric acid, there was a prominent decrease in cell number. DNA synthesis was completely (100%) inhibited by 24 hours. When treated with 500 µM fusaric acid, the majority of the LoVo cells acquired a rounded morphology by 48 hours.

Figure 4A:
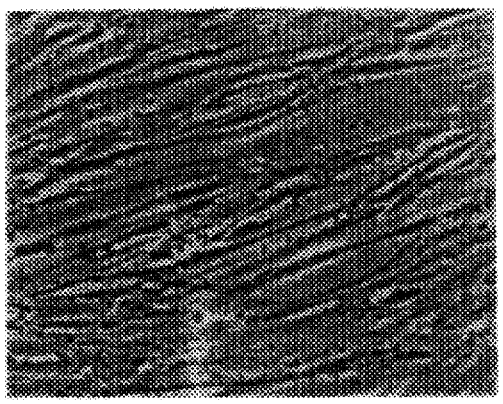
FIG. 4A illustrates the effects of fusaric acid on morphology of WI-38 cells, the cells treated without fusaric acid.
Figure 4B:
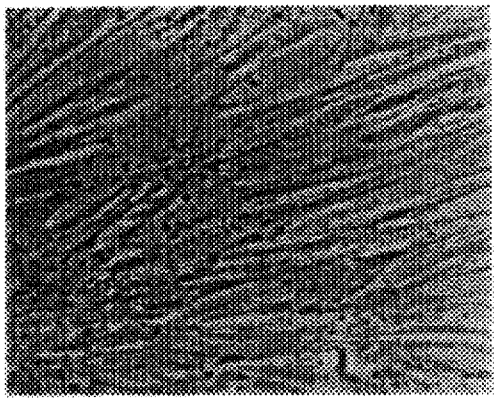
FIG. 4B illustrates the effects of fusaric acid on morphology of WI-38 cells, the cells treated with fusaric acid.
Figure 4C:
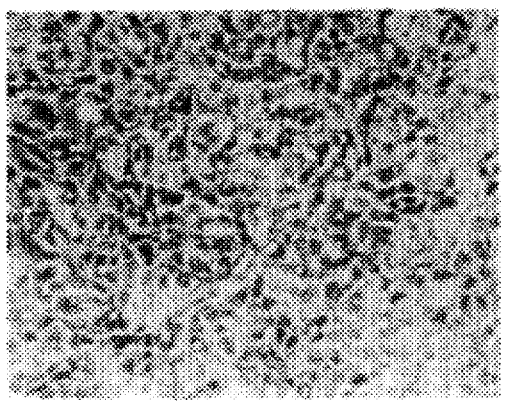
FIG. 4C illustrates the effects of fusaric acid on morphology of LoVo cells, the cells treated without fusaric acid.
Figure 4D:
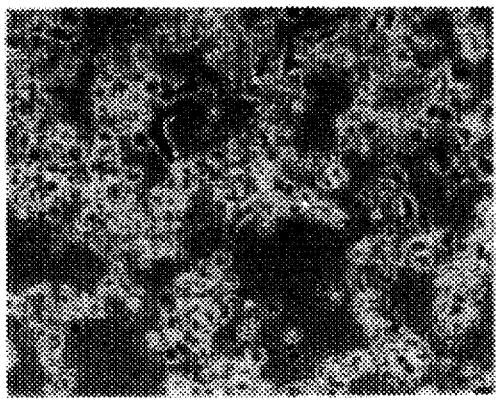
FIG. 4D illustrates the effects of fusaric acid on morphology of LoVo cells, the cells treated with fusaric acid.

As shown in FIG. 4D, most of the cells became granular, showed pronounced cytotoxic effects, many were destroyed, and subsequently detached from the culture dish. These floating cells were not viable. They did not adhere to the substratum and disintegrated after 1 to 3 days when resuspended in fresh medium without fusaric acid. FIG. 4B shows that within 30 hours of treatment there was a 60% decrease in cell number. Following removal of the drug after 30 hours of treatment showed that the cell population continued to decline (~80%) in number up to approximately 100 hours (FIG. 4B). However, after 100 hours, an increase in cell number was noted after 25 additional hours.

As in the case of WI-38, LoVo cell viability after fusaric acid treatment was investigated in logarithmically growing and confluent cells, as shown in Tables 2 and 3. In logarithmically growing LoVo cells, approximately 38% of the attached cells were viable after 30 hours of treatment with fusaric acid. When the cells were treated for 78 hours, only 4.5% of the cell population survived the pronounced cytotoxic actions of fusaric acid. The detach cells showed noticeable cytotoxic and most of them were destroyed at these time points. In confluent cell, fusaric acid showed a significant cytotoxic effect as determined by the fact that only 40% of the cells survived 48 hours of treatment with 500 µM fusaric acid. Thus, LoVo cells are much more sensitive to the cytotoxic actions of fusaric acid in both growing and confluent population of cells in comparison to normal WI-38 cells.

EXAMPLE 4

Effect of Fusaric Acid on Growth and Viability of Human Carcinoma KB Cells.

Figure 3C:
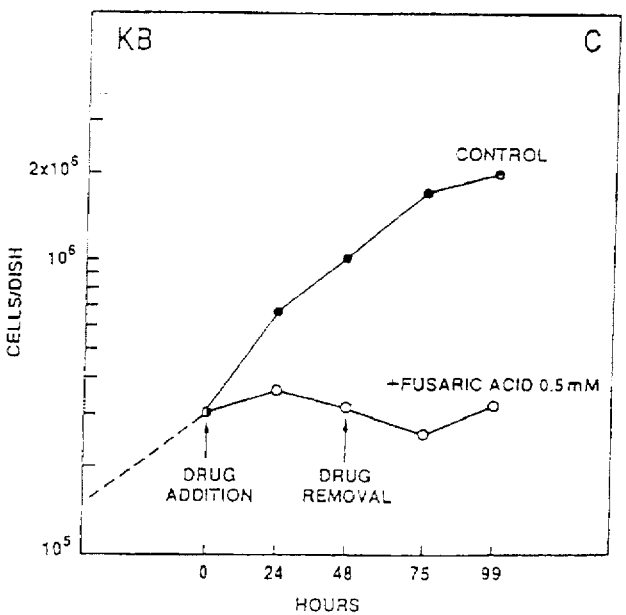
FIG. 3C illustrates the effects of fusaric acid on the growth of KB cells.

FIG. 2C shows that the growth of KB cells was inhibited by fusaric acid (500 µM). After 24 hours of treatment there was no further increase in cell number. As illustrated in FIGS. 3C and 5B, after 24–48 hours in 500 µM fusaric acid, most of the KB cells acquired a more flattened morphology, and no mitotic cells or further increase in cell number were observed. Following 48 hours incubation with fusaric acid (500 µM), normal growth rate was not restored after removal of fusaric acid and the cell number decreased significantly after 27 additional hours in normal media (FIG. 3C). The remaining cells were spread on the substratum in normal manner without any visible mitosis for 27 additional hours after drug removal. However, they resumed growth after 27 hours of removal of fusaric acid (FIG. 3C).

To examine KB cell viability in greater detail, the effects of fusaric acid were studied in logarithmically growing and confluent cells. In logarithmically growing KB cells 70% of the cells were viable after 48 hours in 500 µM fusaric acid. In confluent cell, fusaric acid did not show significant cytotoxic effect, as determined by the fact that 95% of the cells survived 48 hours of treatment with 500 µM fusaric acid (See Table 3, above). Thus, in contrast to LoVo cells, a significant proportion of the population of growing (70%) cells and virtually all (95%) of confluent KB cells resisted the pronounced cytotoxic action of fusaric acid (See Tables 2 and 3, above).

EXAMPLE 5

Effect of Fusaric Acid on Growth and Viability of Human Breast Adenocarcinoma Cells.

Fusaric acid (500 µM) rapidly inhibited human breast adenocarcinoma MDA-468 cell growth. After 12–24 hours of treatment with 500 µM fusaric acid, there was no further increase in cell number. DNA synthesis was completely inhibited (100%) by 24 hr. When treated with 500 µM fusaric acid, the majority of the MDA-468 cells became granular, showed pronounced cytotoxic effects, many were destroyed and subsequently detached from the culture dish. These floating cells were not viable. Within 30 hours of treatment there was a 65% decrease in cell number. Following removal of the drug after 30 hours of treatment showed that the cell population continued to decline in number. After 96 hours, less than 10% of the original population remained attached to the dish and no change in cell number was noted after one additional week.

As in the case of WI-38, MDA-468 cell viability after fusaric acid treatment was investigated in logarithmically growing and confluent cells. In logarithmically growing MDA-468 cells, less than 20% of the attached cells were viable after 30 hours of treatment with fusaric acid. When the cells were treated for 48 hours, only 0.1% of the cell population survived the pronounced cytotoxic actions of fusaric acid. In confluent cells, fusaric acid showed significant cytotoxic effect as determined by the fact that only 10% of the cells survived 48 hours of treatment with 500 µM fusaric acid. Thus, MDA-468 cells are extremely sensitive to the cytotoxic actions of fusaric acid in both growing and confluent population of cells in comparison to normal WI-38 lines studied.

Thus, fusaric acid is effective to reduce and control growth of this common type of human malignancy.

EXAMPLE 6

Effects of fusaric acid on growth and viability of other human carcinoma cell types As in previous examples, the following human cell lines were inhibited by similar concentrations of fusaric acid: Prostatic adenocarcinoma, skin carcinoma, colon carcinoma, liver adenocarcinoma and lung adenocarcinoma. For all these cell types, cell viability decreased by approximately 60% after 48 hours of treatment with fusaric acid.

EXAMPLE 7

Combined effects of fusaric acid and standard chemotherapeutic agents.

Other chemotherapeutic agents such as 5-fluorouracil and/or levamisole in the case of colon adenocarcinoma may be utilized in conjunction with fusaric acid to enhance the effectiveness of therapy. Irreversible cell death and biological alterations induced by fusaric acid also may be enhanced by using agents from the group consisting of anti-cancer antibodies, radioactive isotopes, and chemotherapeutic agents.

The method of using fusaric acid or picolinic acid topically to treat a variety of viral and spontaneous proliferative diseases, as will be described in detail below, can be used in combination with cytotoxic agents selected from the group consisting of chemotherapuetic agents, antibodies, radioactive isotopes, and cytokines (eg. Interferons), vitamin A, for enhanced activity.

EXAMPLE 8

Fusaric Acid effect on cells with increased P-protein activity

Multidrug resistance (MDR) is a formidable obstacle to effective cancer chemotherapy. Studies have indicated that MDR is a phenomenon in which resistance to one drug is associated with resistance to a variety of unrelated drugs. Thus, even when a combination of chemotherapeutics is used, patients may exhibit concurrent resistance to some or all of the drugs, leading ultimately to failure of therapy.

One of the primary contributors to MDR is a glycoprotein denoted P-glycoprotein of molecular weight 170 Kdal, also know as P170. P-glycoprotein or P170 acts as a pump, effectively eliminating chemotherapeutic agents from the cell interior to the extracellular space. Although drug-sensitive cells are destroyed during the initial and subsequent courses of chemotherapy, drug resistance cells, containing elevated levels of P-glycoprotein, emerge, multiply and eventually lead to death of the host.

P-glycoprotein, the product of the mdr-1 gene is a plasma membrane protein. The molecule is composed of 12 transmembrane domains and two binding sites for ATP, which furnishes the energy required for drug elimination. The function of this protein in normal cells is presumably to eliminate naturally occurring toxic compounds. Elevated levels of P-glycoprotein have been associated with multi-drug resistance in numerous malignancies, including: colon carcinoma, breast carcinoma, liver, pancreas, lung carcinoma and other tumors.

From the previous information, it is evident that drugs that are not neutralized by the P-glycoprotein mechanism will be of benefit for chemotherapeutic attack of susceptible and MDR-resistant cells. Of considerably interest for this invention is the data showing that fusaric acid does not induce P170 protein and is effective in controlling growth of cells with high levels of P170 protein. Thus, fusaric acid may have some role in the treatment of tumors which are resistant to MDR-associated drugs.

INHIBITION OF RETROVIRAL mRNA EXPRESSION IN TISSUE CULTURE CELLS BY FUSARIC ACID

EXAMPLE 9

Use of fusaric acid to reduce the if retroviral mRNA levels

By using Kirsten (K) sarcoma retrovirus-transformed NRK cells it was shown in preliminary experiments that fusaric acid reduces the expression of retroviral mRNA levels. Furthermore, it also may be shown that the combination of fusaric acid and interferon-gamma results in a potent inihibition of K sarcoma virus mRNA expression in K-NRK cells.

Identification of fusaric acid as a substance that can inhibit expression of mRNA controlled by a retroviral promoter is a great interest because of the importance of retroviruses, such as the human immunodeficiency virus (HIV), in animal and human disease. Although the biology of K-virus and HIV is different, fusaric acid may be effective in controlling HIV viral expression. Furthermore, the combination of fusaric acid plus interferon-gamma may be much more potent in inhibiting HIV expression in human monocytes and other infected cells. Thus, this inventions is not limited to the effects of fusaric acid in K-NRK, cells but is extended to the actions of this agent in other retrovirally infected human and animal cells.

PREPARATIONS CONTAINING METAL CHELATING PICOLINIC ACID AND DERIVATIVES AND THE TREATMENT AND PREVENTION OF SPECIFIC DISEASE STATES WITH THE PREPARATIONS

EXAMPLE 10

Topical or intravaginal preparation of picolinic acid in a absorption base

A topical or intravaginal preparation of picolinic acid in an absorption base is made by incorporating 0.5% to 50%, preferably 5% to 20% picolinic acid into an absorption base. An absorption base generally is an anhydrous base which has the property of absorbing several times its weight of water to form an emulsion and still retain an ointment-like consistency. Absorption bases may vary in their composition but generally are a mixture of animal sterols with petrolatum, such as Hydrophilic Petrolatum, U.S.P. The most common commercially available products are Eucerin and Aquaphor (Beiersdorf) and Polysorb (Fougera). One preferred embodiment of the topical preparation is made by dissolving 10% picolinic acid in deionized water and then incorporating the solution into an equal amount of Aquaphor, on a wt/wt basis.

EXAMPLE 11

Picolinic acid solution

Picolinic acid can be employed topically or for vaginal installation as a 0.5% to 50%, preferably 5% to 20%, aqueous solution. One preferred embodiment of the solution is prepared by dissolving an appropriate amount of picolinic acid in an appropriate amount of deionized water to form a 10% solution.

EXAMPLE 12

Treatment of ulcerative lesion with topical picolinic acid

A subject horse had a 3 inch diameter ulcerative lesion on the left side of its neck. The lesion had a papillomatous appearance with bleeding at the tips of the papillae. The lesion was progressive, with total loss of hair over the area. The diagnosis was viral disease, i.e. papilloma virus, complicated by fungal infection. The horse was treated with conventional local antibiotic and chemical therapies for about four months. However, the agents used did not modify the course of the disease.

An aqueous solution of 10% picolinic acid in deionized water was applied every other day with a cotton swab over and around the lesion. The treatment continued for 45 days. The course of the regression of the viral lesion was a follows:

1) after 10 days of treatment, the bleeding papillae suffered central necrosis and the borders of the ulcer acquired the aspect of granulomatous proliferating healing tissue;

2) after 20 days of treatment, the healing lesion began to show hair growth in multiple areas; the diameter of the lesion was reduced to approximately 2 inches and appeared flat and clean of debris;

3) after 30 days of treatment, the lesion was about 1 inch in diameter with abundant hair growth on the borders and on the surface of the lesion;

4) at 45 days the lesion resolved with some scar tissue; hair covered all of the area; and 5) after three additional months the horse was observed without evidence of recurring disease.

EXAMPLE 13

Treatment of patients with papilloma virus skin lesions

Picolinic acid and its analogues act by chelating metal ions. In the case of the inhibition of viral replication by picolinic acid, the ion involved is zinc, which is essential to maintain the active structure of zinc finger proteins such as E6 and E7 proteins of the human papilloma viruses essential for viral replication.

Five patients ranging in age from 11 years to 52 years and each having at least one common wart induced by type 4 human papilloma virus was treated with a topical preparation of picolinic acid. The topical preparation was either solution of 10% to 20% picolinic acid in deionized water or a topical ointment wherein 10% picolinic acid is incorporated into Aquaphor, i.e. 1 g of picolinic acid in 10 g of Aquaphor. After seven days of application of the solution or ointment, central necrosis of the wart occurred. After approximately 4 to 6 weeks the warts were gone. It should be noted that there was no significant difference observed in the course of disease between the 10% and 20% solutions. However, faster resolution was seen with the ointment and is believed to be due to the continual contact time imparted by the ointment base.

EXAMPLE 14

Treatment of virus-induced plantar ulcer

A 50 year old patient with recurrent plantar wart of about 2 cm in diameter was treated with topical picolinic acid. The patient, a dermatologist who had difficulty walking because of the pain caused by the ulcer, had experimented with numerous medications for more than three months without any significant results prior to treatment with the picolinic acid. It is relevant to note that many plantar ulcers are transformed into malignant tumors.

The patient was treated with a solution of 10% picolinic acid in deionized water for one week. Central necrosis was noted. He then was treated with 10% picolinic acid in Aquaphor. The ointment was placed on the ulcer and on a patch. The patch was replaced every 24 hours. After an additional three weeks the plantar ulcer resolved.

EXAMPLE 15

Treatment of metastatic disease to the skull from breast cancer

A 73 year old female with metastatic breast cancer to the skin and bone of the skull was treated with a topical preparation of 10% picolinic acid in Aquaphor. The preparation was applied to the cancerous lesions and to a bandage and changed twice daily. The multiple cancer lesions were approximately 1 to 1.5 cm in diameter. The lesions resolved with scar tissue forming after approximately 35 days.

EXAMPLE 16

Treatment of proliferative skin disorders

Several patients suffering from proliferative skin disorders such psoriasis have been included in a recent ongoing study of the anti-proliferative effects of topical picolinic acid. Preliminary information indicates that the picolinic acid has a significant effect in inducing regression of the psoriasis. The patients may be treated with a topical application of approximately 5% to 20% picolinic acid, or a derivative thereof, in an absorption base. Alternatively, the patient may be treated with a solution containing approximately 5% to 20% picolinic acid, or derivative, in deionized water. The topical preparation may be applied twice a day or in an alternative pharmacologically acceptable regimen.

EXAMPLE 17

Treatment of Actinic lesions

Two patients with actinic lesions (average of 5 lesions per patient, each lesion being approximately 3 mm to 5 mm in diameter) were diagnosed as requiring liquid nitrogen removal of the lesions. The patients received a daily application of 10% picolinic acid in Aquaphor. After approximately three weeks of treatment, the lesions were completely cured (eliminated) without any effects on normal skin.

EXAMPLE 18

Use of picolinic acid prophylactically to prevent sexually transmitted diseases

As stated above, it is likely that picolinic acid will interfere with the replication of the retroviruses by chelating zinc and preventing the activity of certain zinc finger proteins. Therefore, a suitable preparation of a chelating material, for example, picolinic acid or derivative may be used for vaginal application to prevent infection with any virus containing zinc finger proteins as an essential component of the viral replicating machinery, i.e. transcription factors. Such viruses include, but are not limited to, human papilloma viruses (E6 and E7 zinc finger proteins) and the AIDS virus (tat protein).

The preparation may be prepared by incorporating approximately 5% to 20% picolinic acid in a suitable base, such as Aquaphor, and instilling the ointment vaginally before coitus. It also may be possible to prepare a douche of approximately 0.5% to 50%, preferably 5% to 20%, picolinic acid in deionized water and used before and after coitus. Such preparations may be used prophylactically to prevent infection with these viruses.

Furthermore, the preparations may be used vaginally to treat the uterine cervix infected with papilloma virus.

A condom containing approximately 5% to 20% picolinic acid or derivative may be used to prevent replication of the viruses in the vaginal and cervical cells in the event the condom fails or ruptures.

It will be appreciated that various changes and modifications may be made in the preparations and methods described and illustrated with out departing from the scope of the appended claims. For example, suitable preparations, other than topical preparations, of metal chelating compounds may be employed for the treatment of adenocarcinomas and squamous cell carcinomas. The preparation may be used alone or in combination with other chemotherapeutic agents. Furthermore, the preparations may be used to treat a wide spectrum of proliferative and viral diseases mediated by zinc finger proteins or other metal ion dependent proteins or enzymes. Therefore, the foregoing specification and accompanying drawings are intended to be illustrative only and should not be view in a limiting sense.

What is claimed is:

1. A method of treating proliferative dermatological diseases by the topical application of picolinic acid.

2. The method of claim 1 further comprising the topical application of a solution of picolinic acid.

3. The method of claim 1 wherein the solution of picolinic acid contains approximately 0.5% to 50% picolinic acid.

4. The method of claim 1 further comprising the topical application of a preparation of picolinic acid in a pharmacologically acceptable absorption base.

5. The method of claim 4 wherein the preparation contains approximately 0.5% to 50% picolinic acid.

6. A method of treating diseases caused by papilloma viruses comprising the application of picolinic acid or a derivative thereof.

7. A method of treating diseases caused by herpes viruses comprising the application of picolinic acid.

8. A method of preventing sexually transmitted diseases by the intravaginal installation of picolinic acid or derivative thereof, wherein said derivative thereof is an acid capable of chelating a metal ion.

9. The method of claim 8 wherein said picolinic acid or derivative thereof is contained in an ointment base.

10. The method of claim 8 wherein the picolinic acid or derivative thereof is contained in a solution.

11. The method of claim 8 wherein the sexually transmitted viral disease is caused by herpes viruses.

12. The method of claim 8 wherein the sexually transmitted viral disease is caused by papilloma viruses.

13. The method of claim 8 wherein the sexually transmitted viral disease is caused by the AIDS virus.

14. A topical or intravaginal preparation of picolinic acid comprising about 0.5% to about 50% picolinic acid, and a liquid vehicle.

15. A topical or intravaginal preparation comprising:
about 0.5% to about 50% of picolinic acid, and
an ointment base.

16. The preparation of claim 15 wherein the ointment base is an absorption base.

17. A method of treating diseases caused by viruses having at least one metal containing protein complex in their physical structure comprising the application of picolinic acid or derivative thereof, said derivative thereof being an acid capable of chelating the metal in the metal-containing protein complex.

18. An antiviral for treating diseases caused by viruses having atleast one metal-containing protein complex in the physical structure thereof comprising picolinic acid or derivative thereof, said derivative thereof being an acid capable of chelating the metal in the metal-containing protein complex.

* * * * *